US006294201B1

(12) United States Patent
Kettelhoit et al.

(10) Patent No.: US 6,294,201 B1
(45) Date of Patent: Sep. 25, 2001

(54) OSMOTIC MEDICAMENT RELEASING SYSTEM

(75) Inventors: Stefan Kettelhoit, Solingen; Ranga-Rao Kanikanti, Leverkusen; Erich Brendel, Solingen, all of (DE); Claus Weisemann, Apex, NC (US); Ernst Chantraine; Michael Eisele, both of Bergisch Gladbach (DE); Patrick Bosché, Odenthal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/530,158

(22) PCT Filed: Oct. 12, 1998

(86) PCT No.: PCT/EP98/06454

§ 371 Date: Apr. 25, 2000

§ 102(e) Date: Apr. 25, 2000

(87) PCT Pub. No.: WO99/21535

PCT Pub. Date: May 6, 1999

(30) Foreign Application Priority Data

Oct. 12, 1997 (DE) .............................................. 197 47 261

(51) Int. Cl.⁷ ................................ A61K 9/24; A61K 9/20; A61K 9/26; A61K 9/14
(52) U.S. Cl. ........................... 424/473; 424/464; 424/469; 424/484; 424/486; 424/488
(58) Field of Search ..................................... 424/464, 473, 424/484, 486, 488, 469

(56) References Cited

U.S. PATENT DOCUMENTS

| Re. 34,990 | * | 7/1995 | Khanna et al. ...................... 424/473 |
| 4,992,278 | | 2/1991 | Khanna ................. 424/473 |
| 5,178,867 | * | 1/1993 | Guittard et al. ..................... 424/473 |
| 5,455,046 | * | 10/1995 | Baichwal ............................ 424/457 |

FOREIGN PATENT DOCUMENTS

| 2175293 | 11/1996 | (CA) | ............................ A61K/31/455 |
| 0277092 | 1/1992 | (EP) | ................................. A61K/9/22 |
| 0740934 | 11/1996 | (EP) | ................................. A61K/9/14 |
| 9640080 | 12/1996 | (WO) | ................................ A61K/9/36 |
| 9739050 | 10/1997 | (WO) | ................................ C08J/3/075 |

* cited by examiner

Primary Examiner—Thurman K. Page
Assistant Examiner—S. Tran
(74) Attorney, Agent, or Firm—Jerrie L. Chiu

(57) ABSTRACT

This invention relates to an orally administered osmotic drug release system that consists of a shell and a core containing a pharmaceutically active substance, as well as a process for its production. The invention relates further to an osmotic drug release system for use as a drug in human beings and animals, as well as the use of the osmotic drug release system in the production of a drug for the treatment and/or prevention of illnesses in human beings and animals.

17 Claims, No Drawings

OSMOTIC MEDICAMENT RELEASING SYSTEM

This application is a 371 PCT/EP98/06454 filed Oct. 12, 1998.

This invention relates to an orally administered osmotic drug release system that consists of a shell and a core containing a pharmaceutically active substance, as well as a process for its production. The invention relates further to an osmotic drug release system for use as a drug in human beings and animals, as well as the use of the osmotic drug release system in the production of a drug for the treatment and/or prevention of illnesses in human beings and animals.

In principle, osmotic drug release systems are known in the state of the art. Osmotic pressure is generally used as the energy source for delivering the active ingredient of a drug to the surrounding medium at a controlled rate. Consequently, these types of systems are referred to as osmotic pumps. A comprehensive overview of osmotic drug release systems can be found in Journal of Controlled Release 35 (1995), 1-21, where a basic distinction is drawn between multiple-chamber systems and single-chamber systems. In its most basic form, the single-chamber system consists of a conventional tablet comprising a shell made of a semi-permeable membrane with an outlet, as well as a core containing the active ingredient in solid form. Following oral administration, water passes into the core through the semi-permeable membrane and dissolves the active ingredient, which is then released through the outlet (U.S. Pat. No. 3,845,770). However, this principle is only suitable for use with highly water-soluble active ingredients, as these are the only active ingredients capable of generating sufficiently high osmotic pressure. Consequently, so-called double-chamber systems ("push-pull" systems) were developed specifically for poorly soluble active ingredients (U.S. Pat. No. 4,111,202; European patent application no. 52 917). However, the production of such two-chamber systems is highly complex in technical terms. Consequently, the single-chamber system possesses a fundamental advantage over multiple-chamber systems. To utilize the advantages of the single-chamber system for poorly soluble drugs while achieving sufficient osmotic pressure in the interior of the tablet, single-chamber systems were proposed in which a core consists of the active ingredient and certain polymeric swelling agents which, upon the addition of water, expand through the outer semi-permeable membrane and are released together with the active ingredient, which is partially suspended in the swelling agent. The selection of certain polymeric swelling agents is of decisive importance in this system, as certain swelling agents, as has been described in EP-A-0 277 092, such as polyvinyl pyrrolidone, polyethylene oxide or polymethylacrylate produce so much expansion pressure that the semi-permeable shell membrane bursts open completely after a short time and the active ingredient is released within a short period of time instead of being released in a delayed or controlled manner, as desired. Thus, to solve this problem, EP-A-0 277 092 provides for a specific selection of hydrophilic polymeric swelling agents, namely a mixture of a vinyl pyrrolidone - vinyl acetate copolymer and an ethylene oxide homopolymer.

WO 96/40080 claims generic protection for osmotic single-chamber systems comprising a core made of a pharmaceutical active ingredient, a water-soluble osmotic agent and a water-expandable polymer. However, as has already been specified in EP-A-0 277 092, not all polymeric hydrophilic swelling agents are suited for use in these single-chamber systems, and a careful selection must be made to ensure that the active substance is released from the single-chamber system in a controlled manner, as desired. In the concrete forms of execution of WO 96/40080, polyethylene oxide and cellulose, or derivatives thereof, are among the materials used as water-expandable polymers.

An osmotic drug release system with controlled, i.e., generally delayed release, that consists of a single-chamber system should, in principle, allow for maximum release of the active ingredient without the outlet being torn open during release and resulting in uncontrolled release of the active ingredient. However, a common problem among singlehamber systems is that a substantial portion of the active ingredient remains in the tablet, as insufficient osmotic pressure is generated in the interior of the tablet to fully release the active ingredient. Thus, a disadvantage of the systems described above is that they do not fully release the active substance from the shell membrane and through the outlet, so that relatively large component of the active substance is not absorbed and is excreted unused. However, the use of a water-expandable polymer that generates substantial osmotic pressure may result in the tablet being torn open or even bursting, thus preventing delayed, controlled release from being achieved.

Another problem commonly found in osmotic drug release systems known in the art is that the uncoated tablet cores lack sufficient mechanical stability, which makes them difficult to coat.

In principle, an osmotic drug release system should be easily manufactured, consist of reasonably priced and pharmacologically tolerable materials, and allow for the release of the active ingredient in an advantageous manner.

Surprisingly, it was found that the use of a combination of two specific hydrophilic water-expandable polymers as core components, at specific weight proportions, is particularly suited for achieving the aforementioned desired attributes of an osmotic single-chamber drug release system that contains a pharmaceutically active substance, preferably a dihydropyridine as its active ingredient. The inventors of this invention found that a combination of the heteropolysaccharide xanthan and a vinyl pyrrolidone—vinyl acetate copolymer as water-expandable polymers in specific weight concentrations allows for the virtually complete release of the active substance from the shell without resulting in the outlet being torn open and the active ingredient being released in an uncontrolled manner.

Without relying on theoretical constraints, it is assumed that the highly favorable release properties of the combination between xanthan and the vinyl pyrrolidone—vinyl acetate copolymer are due, in particular, to the fact that it forms structurally viscous solutions, the viscosity of which decreases during flow in response to increasing transverse strain. Apparently, this allows for especially uniform release of the active substance from the outlet without the membrane being torn open, so that the active substance is released uniformly and almost completely over a relatively long period of time.

When used as a water-expandable polymer, xanthan also possesses the advantage of being easier to handle than the polyethylene oxides used in EP-A-0 277 092 and WO 96/40080, as it does not induce the so-called TOMS effect (reduction in frictional resistance). Another advantage associated with the use of xanthan in comparison with the use of polyethylene oxide as a water-expandable polymer consists in the fact that polyethylene oxides are generally only wet-granulated with organic solvents (as, for example, in EP-A-0 277 092), so that explosion protection measures must be taken during production; alternatively, tablets must be produced in a dry state (WO 96/40080), which results in the known disadvantages of dry tablet-making, such as poor flow properties of the mixture of core components, dust development and a low degree of hardness of the tablet core.

This invention overcomes the problems of the state of the art described above by presenting an osmotic drug release system that consists of:

a shell consisting of a material that is water-permeable but impermeable to the components of the core, with at least one opening, and a core, containing 15 to 35% in weight of a pharmaceutically active substance 20 to 50% in weight of xanthan 10 to 30% in weight of a vinyl pyrrolidone—vinyl acetate copolymer in which, if necessary, the balance of the 100% in weight is made up by at least one component selected from a group consisting of other hydrophilic expandable polymers, osmotically active additives and pharmaceutically acceptable additive materials, the percent in weight figures refer to the total weight of the core components, and the sum of the core components totals 100%.

The shell of the osmotic drug release system consists of a material that is water-permeable but impermeable to the components of the core. Such shell materials are known in principle and described, for example, EP-A-0 277 092. Suitable materials for production of the shell consist, for example, of polymeric substances known in the literature that are not metabolized in the gastrointestinal tract, i.e., are excreted without having been altered (see U.S. Pat. Nos. 3,916,899 and 3,977,404). For example, acylated cellulose derivatives (cellulose esters) are used which are substituted one to three times by acetyl groups or one to two times by acetyl groups and once further by an acetyl residue that differs from acetyl, e.g., cellulose acetate, cellulose triacetate, cellulose acetate ethyl carbamate, cellulose acetate phthalate, cellulose acetate methyl carbamate, cellulose acetate succinate, cellulose acetate dimethyl amino acetate, cellulose acetate ethyl carbonate, cellulose acetate chloric acetate, cellulose acetate ethyloxylate, cellulose acetate methyl sulfonate, cellulose acetate butyl sulfonate, cellulose acetate propionate, cellulose acetate diethyl amino acetate, cellulose acetate octate, cellulose acetate laurate, cellulose acetate p-toluol sulfonate, cellulose acetate butyrate and other cellulose acetate derivatives, as well as agaric acetate and amylose acetate. Materials suitable for use as a semi-permeable membrane also include ethyl cellulose and polymeric epoxides, copolymers of alkylene oxide and alkyl glycidylethers, polyglycols and poly-lactic acid derivatives, as well as other derivatives thereof Mixtures of acrylates that are, in fact, water-insoluble (e.g., a copolymerisate of acrylic acid ethyl ester and methacrylic acid methyl ester) may also be used. If necessary, a light-protectant coating can be applied to the shell. Suitable materials for the light-protectant coating include polymers, such as hydroxypropylcellulose and hydroxypropyhnethylcellulose, in combination with suitable plasticizers, such as polyethylene glycol, and pigments, such as titanium dioxide and iron oxides.

The quantities and the components used in the production of the shell of the osmotic drug release system influence the rate of penetration of the gastrointestinal fluid in a known manner. As a rule, the rate of penetration of the gastrointestinal fluid decreases as the amount of coating increases.

The shell of the osmotic drug release system in this invention has at least one opening, or passage, through which the active ingredient and other core components gradually emerge. The opening is cut into the shell by means of laser drilling, mechanical drilling or a punching mechanism. There may be one or more openings in the shell. The preferable size of the opening is 0.2 to 1.6 mm or, more preferably, 0.4 to 1.2 mm. The structure and means of producing the opening are known in the art and described, for example, in U.S. Pat. Nos. 4,063,064, 4,088,864 and 3,916,899, as well as in EP-B-0277092.

The core of the osmotic drug release system in this invention contains, or consists primarily of, the following components:

15 to 35% in weight of a pharmaceutically active substance 20 to 50% in weight of xanthan 10 to 30% in weight of a vinyl pyrrolidone—vinyl acetate copolymer in which, if necessary, the balance of the 100% in weight is made up by at least one component selected from a group consisting of other hydrophilic expandable polymers, osmotically active additives and pharmaceutically acceptable additive materials, the percent in weight figures refer to the total weight of the core components, and the sum of the core components totals 100%.

Preferably, the core consists of:

20 to 30% in weight of a pharmaceutically active substance 25 to 40% in weight of xanthan 10 to 20% in weight of a vinyl pyrrolidone—vinyl acetate copolymer in which, if necessary, the balance of the 100% in weight is made up by at least one component selected from a group consisting of other hydrophilic expandable polymers, osmotically active additives and pharmaceutically acceptable additive materials, the percent in weight figures refer to the total weight of the core components, and the sum of the core components totals 100%.

Other components customarily used in osmotic drug release systems may also be included, provided their presence has no adverse effect on resolution of the problem described initially.

The active ingredient found in the core is a pharmaceutically active substance preferably a sparingly soluble active substance having a maximal solubility of $\leq 1$ g in 1000 g of water, especially such active substances wich are still absorbed in the colon, particularly such an active substance taken from the known class of dihydropyridines, as described, for example, in EP-A-0071819, e.g., nifedipine and nisoldipine. They act as calcium antagonists and are used as cardiovascular agents in the indication of high blood pressure, as well as in the treatment and prevention of ischemic brain disorders.

The use of nifedipine is especially preferable.

The amount of the active substance present in the core of the osmotic drug release system in this invention is 15 to 35% in weight, preferably 20 to 30% in weight, and most preferably 19 to 23% in weight, as measured against the total mass of core components.

The hydrophilic water-expandable polymer xanthan is one of the main components of the core of the osmotic drug release system. It is an anionic heteropolysaccharide available commercially, for example, under the brand name Rhodigel® (manufactured by Meyhall).

In a preferred form of execution, the xanthan has a particle size of less than 800 $\mu$m. In some cases, a particle size greater than 800 $\mu$m may lead to a deterioration in release properties. In a particularly preferred form of execution, the particle of the xanthan is less than 500 μm.

The amount of xanthan is 20 to 50% in weight, preferably 25 to 40% in weight, and most preferably 28 to 32% in weight, as measured against the total mass of core components.

The vinyl pyrrolidone—vinyl acetate copolymer is another main component of the core of the osmotic drug release system in this invention. This copolymer is known in the art and can be manufactured using any mixture of the monomer ingredients. As an example, the preferred commercially available product, Kollidon® VA64 (manufactured by BASF), is a 60:40 copolymerisate. Its average molecular weight Mw, as determined by light-scatter testing, generally ranges from about 45,000 to 70,000. The amount of vinyl pyrrolidone—vinyl acetate copolymer in the core of the osmotic drug release system in this invention is 10 to 30% in weight, preferably 10 to 20% in weight, and most preferably 15 to 20% in weight, as measured against the total mass of core components. This results in a preferred weight ratio of xanthan to vinyl pyrrolidone—vinyl acetate copolymer between 5:1 and 2:3.

Preferably, the osmotic drug release system in this invention contains only xanthan and the vinyl pyrrolidone—vinyl acetate copolymer as water-expandable polymers and core components.

In a particularly preferred form of execution of the invention, the osmotic drug release system contains at least one osmotically active additive and/or at least one pharmaceutically acceptable additive material.

In the above case, the core of an osmotic drug release system preferably contains:

20 to 30%/o in weight of an active substance 25 to 40% in weight of xanthan 10 to 20% in weight of a vinyl pyrrolidone—vinyl acetate copolymer 10 to 30% in weight of an osmotically active substance 8 to 20% in weight of at least one pharmaceutically acceptable additive material with the percent in weight figures referring to the total weight of the core components, and the sum of the core components totaling 100%.

Although it is preferable that the osmotic drug release system in this invention only contain xanthan and the vinyl pyrrolidone—vinyl acetate copolymer as water-expandable polymers and core components, if necessary the core may contain other hydrophilic expandable polymers, such as hydroxypropylcellulose, hydroxypropylmethylcellulose, sodium carboxy methyl cellulose, and polyacrylic acids or their salts.

Any additional hydrophilic expandable polymers in the core are present in the osmotic drug release system in this invention in amounts that have no adverse effect on resolution of the problem described initially.

However, the hydrophilic water-expandable polymers used in this invention do not include polyethylene oxide (polyethylene glycol), i.e., the core of the osmotic drug release system in this invention is free of polyethylene oxide additives.

In principle, the optional osmotically active additives in the core of the osmotic drug release system in this invention are not subject to restrictions. Any water-soluble substance can be used whose use is considered unobjectionable in pharmaceutics, such as the water-soluble process materials listed in pharmacopeia, in "Hager" or in "Remington Pharmaceutical Science". Especially suitable materials include water-soluble salts of anorganic or organic acids or non-ionic organic substances that are highly water-soluble, such as carbohydrates, particularly sugar, or amino acids. For example, the osmotically active additives selected may consist of inorganic salts, such as chlorides, sulfates, carbonates and bicarbonates of alkaline or earth alkaline metals, such as lithium, sodium, potassium, magnesium, calcium and phosphate, hydrogen or dihydrogen phosphates, acetate, succinate, benzoate, citrate or citric ascorbate. Other possible substances include pentoses, such as arabinose, ribose or xylose, hexoses, such as glucose, fructose, galactose or mannose, disaccharides, such as sucrose, maltose or lactose, or trisaccharides, such as raffinose. The water-soluble amino acid include glycine, leucine, alanine and methionine. The use of sodium chloride is particularly preferred. The preferable concentration of these osmotically active additives is 10 to 30% in weight, while the most preferable concentration is 15 to 20% in weight, as measured against the total mass of core components.

The core of the osmotic drug release system in this invention may also contain one or more pharmaceutically acceptable additive materials selected from among the following: buffer materials, such as sodium bicarbonate, bursting agents, such as sodium carboxy methyl starch, lubricants, such as magnesium stearate, tablet-making process materials, protective colloids, such as those described in EP-B-0277092, p. 5, lines 10–25, softeners, such as those described in EP-B-0277092, p. 5, lines 29–32, surfactants, such as those described in EP-B-0277092, p. 5, lines 33–44, and carrier materials, such as those described in EP-B-0277092, p. 5, lines 45–47.

In a very particularly preferred form of execution of this invention, the core contains:

19 to 23% in weight of an active substance 28 to 32% in weight of xanthan 15 to 20% in weight of a vinyl pyrrolidone—vinyl acetate copolymer 15 to 20% in weight of sodium chloride 5 to 7% in weight of sodium bicarbonate 6 to 9% in weight of sodium carboxy methyl starch <1% in weight of magnesium stearate with the percent in weight figures referring to the total weight of the core components, and the sum of the core components totaling 100%.

The osmotic drug release system in this invention may have been described in various forms, as, for example, in EP-B-0277092, p. 6, lines 7–14. It is preferably available in tablet form.

The invention also relates to a process for the production of the osmotic drug release system according to invention, in which the components of the core are mixed together, possibly wet- or dry-granulated, and made into tablets, with the resulting core being coated with the shell. Wet granulation often improves the wettability of the components of the tablet core, allowing the incoming gastrointestinal fluid to penetrate the core more easily, which often leads to faster and more complete release of the active ingredient. Consequently, wet granulation is preferred.

The osmotic drug release system according to invention is used for the treatment and/or prevention of illnesses in human beings and animals, such as circulatory diseases, infections, inflammatory diseases, pains, asthma, cancer, malaria, thrombosis, diabetis, arrhythmics of the heart, hypoglycaemics, mycosis, depressions, diseases of the salt- and fluid-balance in the body, diseases of the nutritive metabolism e.g. disturbances of the glycaemic metabolism, coronary heart disease, high blood pressure and cerebral performance disorders, as well as for therapy of neurological deficits following subarachnoid hemorrhage. The use of the osmotic drug release system in this invention for treatment of high blood pressure and coronary heart disease is particularly preferred.

EXAMPLES 1 and 2 (tablets with dry-granulated components)

Composition

Core

|  | 1 | 2 |
|---|---|---|
| Nifedipine | 36.00mg | 36.00mg |
| Xanthan (Rhodigel ®, commercial product, Meyhall) | 50.96mg | 50.96mg |
| Copolyvidone (Kollidon ® VA64, commercial product, BASF, vinyl pyrrolidone - vinyl acetate copolymer) | 29.45mg | 29.45mg |
| Sodium chloride | 28.71mg | 28.71mg |
| Sodium bicarbonate | 10.15mg | 10.15mg |
| Sodium carboxy methyl starch | 12.74mg | 12.74mg |
| Aerosil | 0.85mg | 0.85mg |
| Magnesium stearate | 0.68mg | 0.68mg |
| Shell (osmotic membrane) | | |
| Cellulose acetate | 8.45mg | 11.40mg |
| Polyethylene glycol 3350 | 0.45mg | 0.60mg |
| Approximate tablet weight | 178.5 mg | 181.6 mg |
| Tablet format | 6r9 mm | 6r9 mm |

Production Process

Nifedipine, Kollidon® VA64 (70% in weight of the above mass), Rhodigel®, sodium chloride and sodium bicarbonate were mixed together and then dry-granulated. The granulate was subsequently made into tablets. The tablet cores were coated with an organic coating containing the components of the osmotic membrane. The coated tablets were subsequently dried. The diameter of the resulting tablets was 6 mm.

Subsequently, an opening of approx. 800 μm in diameter was made into each tablet with a hand drill.

Examples 3 and 4 (tablets with wet-granulated components)

Composition

Core

|  | 1 | 2 |
|---|---|---|
| Nifedipine | 36.00mg | 36.00mg |
| Xanthan (Rhodigel ®, commercial product, Meyhall) | 50.96mg | 50.96mg |
| Copolyvidone (Kollidon ® VA64, commercial product, BASF, vinyl pyrrolidone - vinyl acetate copolymer) | 29.45mg | 29.45mg |
| Sodium chloride | 28.71mg | 28.71mg |
| Sodium bicarbonate | 10.15mg | 0.15mg |
| Sodium carboxy methyl starch | 12.74mg | 12.74mg |
| Aerosil | 0.90mg | 0.90mg |
| Magnesium stearate | 0.50mg | 0.50mg |

Shell (osmotic membrane)

| Cellulose acetate | 7.50 mg | 9.40 mg |
|---|---|---|
| Polyethylene glycol 3350 | 0.40 mg | 0.50 mg |
| Approximate tablet weight | 177 mg | 179 mg |
| Tablet format | 6r9 mm | 7r10 mm |

Production Process

Rhodigel®, sodium chloride, sodium bicarbonate and sodium carboxy methyl starch were mixed together and then wet-granulated with a suspension of nifedipine and Kollidon® VA64 in water. The granulate was then mixed with aerosil and magnesium stearate. The mixture was subsequently made into tablets. The tablet cores were coated with an organic coating containing the components of the osmotic membrane. The coated tablets were subsequently dried. The diameter of the resulting tablets was 6 mm and 7 mm, respectively.

Two openings, each with a diameter of approx. 600 μm, were subsequently made into each tablet with a hand drill.

Reference Example 1 (corresponds to example 3 in EP-A-0277092)

Composition

Core

| Nifedipine | 50.00mg |
|---|---|
| Polyox coagulant | 20.00mg |
| Copolyvidone (Kollidon ® VA64, commercial product, BASF, vinyl pyrrolidone - vinyl acetate copolymer) | 18.00mg |
| Sodium chloride | 20.00mg |
| Magnesium stearate | 2.00mg |

Shell (osmotic membrane)

| Cellulose acetate | 11.20 mg |
|---|---|
| Polyethylene glycol 4000 | 1.50 mg |
| Approximate tablet weight | 122.7 mg |
| Tablet format | 7r10 mm |

Production Process

Nifedipine, polyox coagulant, Kollidon® VA64, sodium chloride and magnesium stearate were mixed together. However, to avoid the use of organic solvents, the mixture was then made into tablets without prior granulation. The tablet cores were coated with an organic coating containing the components of the osmotic membrane. To avoid the use of chlorinated carbohydrates, cellulose acetate type 398–10 was used instead of cellulose acetate type 320S. The coated tablets were subsequently dried. The diameter of the resulting tablets was 7 mm.

Subsequently, an opening of approx. 800 μm in diameter was made into each tablet with a hand drill.

Reference Example 2 (corresponds to example 1 in WO-96/40080)

Composition

Core

| | |
|---|---|
| Nifedipine | 33.00 mg |
| Polyox WSR 303 | 27.50 mg |
| Polyox WSR N80 | 55.00 mg |
| Sodium carboxy methyl starch | 82.50 mg |
| Lactose | 74.25 mg |
| Magnesium stearate | 2.75 mg |

Shell (osmotic membrane)

| | |
|---|---|
| Cellulose acetate | 12.48 mg |
| Polyethylene glycol 400 | 0.78 mg |
| Sucrose micr. | 1.56 mg |
| Triacetin | 0.78 mg |
| Approximate tablet weight | 291 mg |
| Tablet format | 9r15 mm |

Production Process

Nifedipine, Polyox WSR 303, Polyox WSR N80, sodium carboxy methyl starch, lactose and magnesium stearate were mixed together. The mixture was then made into tablets.

The resulting tablet cores were very soft, which made further processing very difficult. The tablet cores were coated with an organic coating containing the components of the osmotic membrane. The coated tablets were subsequently dried. The diameter of the resulting tablets was 9 mm. Subsequently, an opening of approx. 800 $\mu$m in diameter was made into each tablet with a hand drill. The release quantities listed for example 1 in WO-96/40080, as depicted in FIG. 1 in WO-96140080, were not observed under the test conditions described below.

Using "device 2" in USP XXIII (The United States Pharmacopeia USP XXIII 1995, pages 1791 to 1792), which employs the paddle method, the osmotic drug release systems produced in the examples and reference examples were tested to determine their release properties. To this end, active ingredient release was measured using conventional release equipment manufactured by the ERWEKA company. In accordance with the German Pharmacopeia, 9th edition, the tablets were incubated in buffer pH=6.8 (10%), with surfactant added at 37° C., and at 100 rpm. Within 24 hours, the tablets had released the active ingredient as shown in the table. The release quantities in the table are expressed as percentage of the amount of active ingredient released in relation to the total amount of active ingredient initially present in the core.

Table: Release of active ingredient from tablets in accordance with examples 1–4 and from tables in reference examples 1–2.

The results indicate that the osmotic drug release system according to invention almost completely releases the active ingredient within the relevant time period, depending on the targeted release rate. In contrast, the osmotic drug release systems known in the art release the active ingredient incompletely by the end of the release period. This is based on the assumption that, after a period of 24 hours, there is no longer any release in absorption-relevant locations in the gastrointestinal tract and that the osmotic drug release system has reached its release plateau. The examples according to invention, examples 1 and 2, on the one hand, and examples 3 and 4, on the other hand, illustrate the effects of wet granulation in comparison to dry granulation. As explained earlier, wet granulation often improves the wettability of the components of the tablet core, allowing the incoming gastrointestinal fluid to penetrate the core more easily, which results in faster and more complete release of the active ingredient. Consequently, wet granulation is preferred. Essentially, the application of wet granulation procedures is only made possible by the use of the special water-expandable polymers in the osmotic drug release system according to invention which, unlike the polyethylene oxides used in the state of the art, do not require organic solvents. A comparison among the examples according to invention, examples 1 and 2, on the one hand, and examples 3 and 4, on the other hand, shows that greater amounts of shell coating result in a certain amount of delay (lag time) at the beginning of the release period, and that the release rate is slowed as a result of the slow rate of gastrointestinal fluid penetration. Regardless of the amount of coating applied, however, release volumes equalize over time in the examples according to invention.

A comparison between example 2 of the invention and reference example 1 shows that, given roughly equivalent coating amounts and coating composition, as well as comparable production procedures (dry granulation vs. direct tablet-making), the osmotic drug release system according to invention provides significantly greater ultimate release at approximately equal initial release rates. This means that the osmotic drug release system according to invention continues to release the active ingredient at a relatively high release rate, even at a later point at which release of the active ingredient in the osmotic drug release system used in the reference example has virtually come to a halt. This means that a substantial portion of the active ingredient in the reference example remains in the tablet and is thus excreted without having been used. A low release rate at a later point during the release period was also observed in reference example 2.

What is claimed is:

1. Osmotic drug release system comprising:
   (a) a shell comprising a material that is water-permeable but inpermeable to the components of the core, with at least one opening, and
   (b) a core, comprising

| Release | Example 1 | Example 2 | Example 3 | Example 4 | Reference example 1 | Reference example 2 |
|---|---|---|---|---|---|---|
| 240 min. | 12.5% | 10% | 32.5% | 30.8% | 5% | 13.6% |
| 480 min. | 41.7% | 30% | 67.5% | 64.5% | 22% | 33.6% |
| 720 min. | 57.5% | 53.3% | 76.7% | 75.8% | 37% | 48.2% |
| 960 min. | 65% | 60.8% | 81.7% | 80.8% | 45% | 54.5% |
| 1440 min. | 70% | 71.7% | 87.5% | 86.7% | 51% | 62.7% |

15 to 35% in weight of a pharmaceutically active substance 20 to 50% in weight of xanthan 10 to 30% in weight of a vinyl pyrrolidone—vinyl acetate copolymer wherein additional components selected from a group consisting of other hydrophilic expandable polymers, osmotically active additives and pharmaceutically acceptable additive materials may also be contained in said core so that the sum of the core components totals 100% in weight, wherein the percent in weight figures refer to the total weight of the core components.

2. Osmotic drug release system according to claim 1, which includes a core comprising:

(a) 20 to 30% in weight of a pharmaceutically active substance (b) 25 to 40% in weight xanthan (c) 10 to 20% in weight of a vinyl pyrrolidone—vinyl acetate copolymer wherein additional components selected from a group consisting of other hydrophilic expandable polymers, osmotically active additives and pharmaceutically acceptable additive materials may also be contained in said core so that the sum of the core components totals 100% in weight, wherein the percent in weight figures refer to the total weight of the core components.

3. Osmotic drug release system according to claim 1 characterized in that the core contains at least one osmotically active additive.

4. Osmotic drug release system according to claim 1 characterized in that the core contains at least one osmotically active additive, as well as at least one pharmaceutically acceptable additive material.

5. Osmotic drug release system according to claim 1 which includes a core comprising:

20 to 30% in weight of a pharmaceutically active substance 25 to 40% in weight of xanthan 10 to 20% in weight of a vinyl pyrrolidone—vinyl acetate copolymer 10 to 30% in weight of an osmotically active substance 8 to 20% in weight of at least one pharmaceutically acceptable additive material with the percent in weight figures referring to the total weight of the core components, and the sum of the core components totaling 100%.

6. Osmotic drug release system according to claim 1 characterized in that the active ingredient is a sparingly soluble active substance.

7. Osmotic drug release system according to claim 1 characterized in that the active ingredient is an active substance which is still absorbed in the colon.

8. Osmotic drug release system according to claim 1 characterized in that the active ingredient is a dihydropyridine.

9. Osmotic drug release system according to claim 1 characterized in that the active ingredient is nifedipine.

10. Osmotic drug release system according to claim 1 characterized in that the osmotically active additive is sodium chloride.

11. Osmotic drug release system according to claim 1 characterized in that the pharmaceutically acceptable additive material is selected from the group consisting of pharmaceutically acceptable buffer materials, pharmaceutically acceptable lubricants, pharmaceutically acceptable disintegrants, and pharmaceutically acceptable tablet-making process materials.

12. Osmotic drug release system according to claim 11, characterized in that the pharmaceutically acceptable buffer material is sodium bicarbonate, the pharmaceutically acceptable lubricant is magnesium stearate, the pharmaceutically acceptable disintegrant agent is sodium carboxy methyl starch, and a pharmaceutically acceptable tablet-making process material.

13. Osmotic drug release system according to claim 1 which includes a core comprising:

19 to 23% in weight of a pharmaceutically active substance 28 to 32% in weight of xanthan 15 to 20% in weight of a vinyl pyrrolidone—vinyl acetate copolymer 15 to 20% in weight of sodium chloride 5 to 7% in weight of sodium bicarbonate 6 to 9% in weight of sodium carboxy methyl starch <1% in weight of magnesium stearate with the percent in weight figures referring to the total weight of the core components, and the sum of the core, components totaling 100%.

14. Osmotic drug release system according to claim 1 characterized in that it is present in tablet form.

15. Procedure for the production of the osmotic drug release system according to claim 1 characterized in that the components of the core are mixed together, possible wet-granulated or dry-granulated, and made into tablets, and that the resulting core is coated with the shell.

16. Osmotic drug release system according to claim 1 for use as a drug in human beings and animals.

17. A method of treating high blood pressure, coronary heart disease, or cerebral performance disorders, and for therapy of neurological deficits following subarachnoid hemorrhage, comprising administering to a patient in need thereof an osmotic drug release system according to claim 1.

* * * * *